(12) United States Patent
Sinha

(10) Patent No.: US 9,427,269 B2
(45) Date of Patent: Aug. 30, 2016

(54) LOCKING SCREWS AND PLATES

(75) Inventor: Amit Sinha, Fort Washington, PA (US)

(73) Assignee: GENOSSIS LLC, Fort Washington, PA (US)

( * ) Notice: Subject to any disclaimer, the term of this patent is extended or adjusted under 35 U.S.C. 154(b) by 246 days.

(21) Appl. No.: 14/004,480

(22) PCT Filed: Mar. 14, 2012

(86) PCT No.: PCT/US2012/029018
§ 371 (c)(1),
(2), (4) Date: Dec. 20, 2013

(87) PCT Pub. No.: WO2012/125691
PCT Pub. Date: Sep. 20, 2012

(65) Prior Publication Data
US 2014/0094856 A1    Apr. 3, 2014

Related U.S. Application Data

(60) Provisional application No. 61/452,216, filed on Mar. 14, 2011, provisional application No. 61/565,527, filed on Dec. 1, 2011.

(51) Int. Cl.
| A61B 17/80 | (2006.01) |
| A61B 17/86 | (2006.01) |
| A61B 17/70 | (2006.01) |

(52) U.S. Cl.
CPC ....... *A61B 17/8052* (2013.01); *A61B 17/7059* (2013.01); *A61B 17/8042* (2013.01); *A61B 17/8047* (2013.01); *A61B 17/8625* (2013.01)

(58) Field of Classification Search
None
See application file for complete search history.

(56) References Cited

U.S. PATENT DOCUMENTS

| 5,601,553 A * | 2/1997 | Trebing ................. A61B 17/15 411/399 |
| 2005/0070904 A1 | 3/2005 | Gerlach et al. |
| 2008/0021477 A1 | 1/2008 | Strnad et al. |
| 2008/0200955 A1 | 8/2008 | Tepic |
| 2008/0208259 A1 | 8/2008 | Gilbert et al. |

OTHER PUBLICATIONS

International Search Report and Written Opinion for International Patent Application PCT/US2012/029018 dated Jun. 20, 2012.

* cited by examiner

*Primary Examiner* — Sameh Boles
(74) *Attorney, Agent, or Firm* — Morgan, Lewis & Bockius LLP

(57) ABSTRACT

A screw is configured to be inserted into an aperture of a plate. The screw comprises a head, a neck that extends distally from the head and having a diameter, a shoulder that extends distally from the neck and has a diameter, and a shaft that extends distally from the shoulder and has a thread, a major diameter and a minor diameter. The diameter of shoulder is larger than the diameter of the neck and larger than the minor diameter of the shaft.

13 Claims, 7 Drawing Sheets

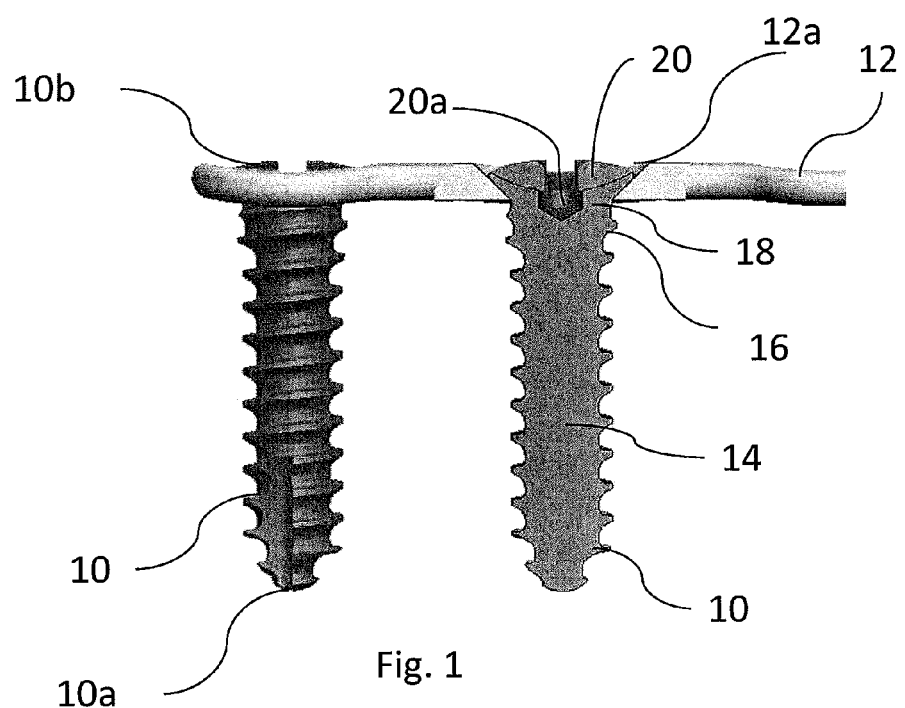
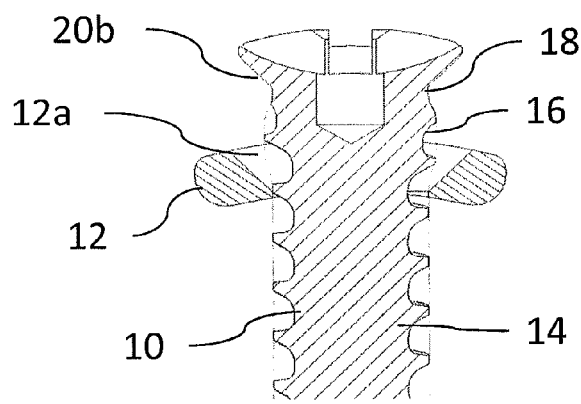
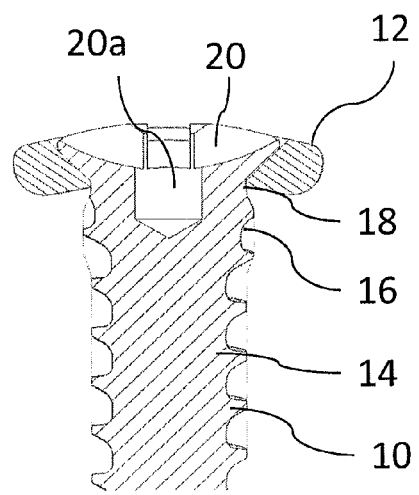
Fig. 1
Fig. 2A
Fig. 2B

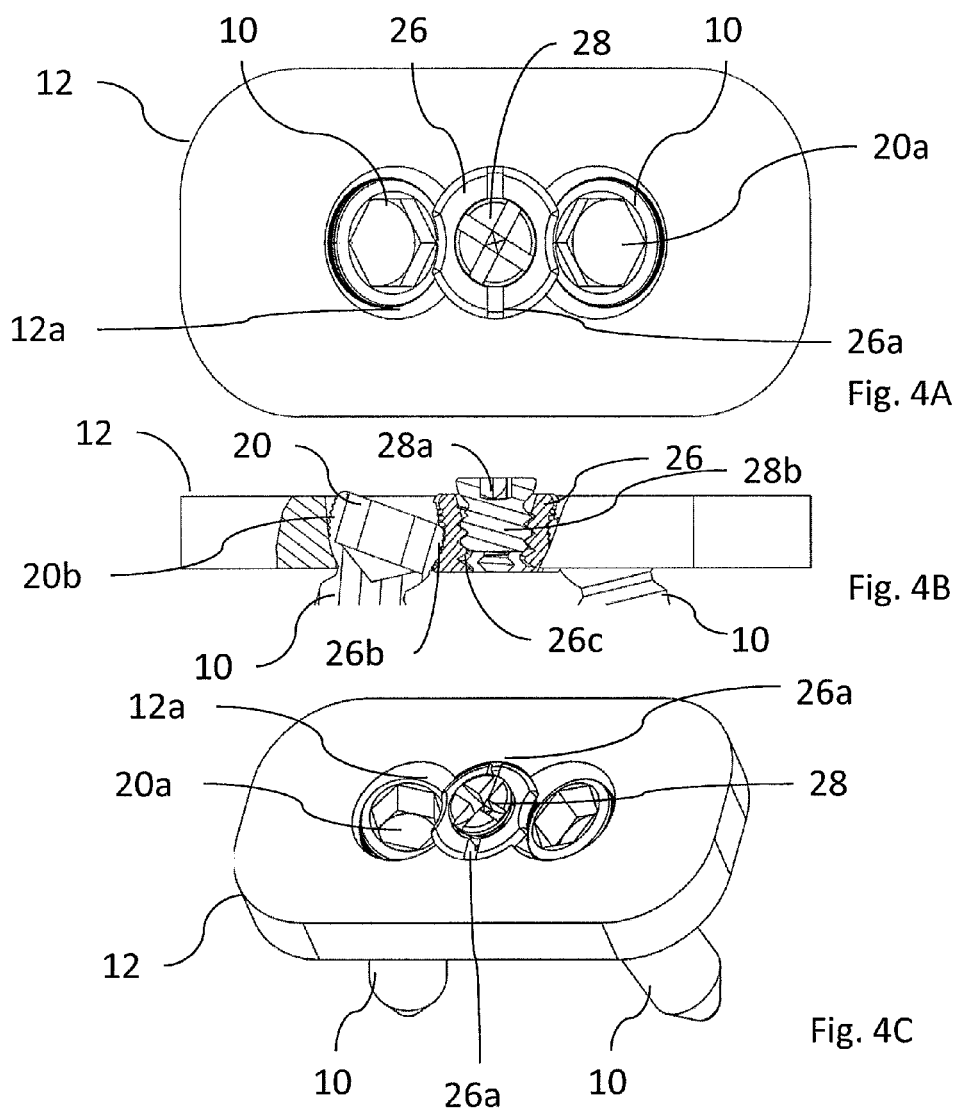

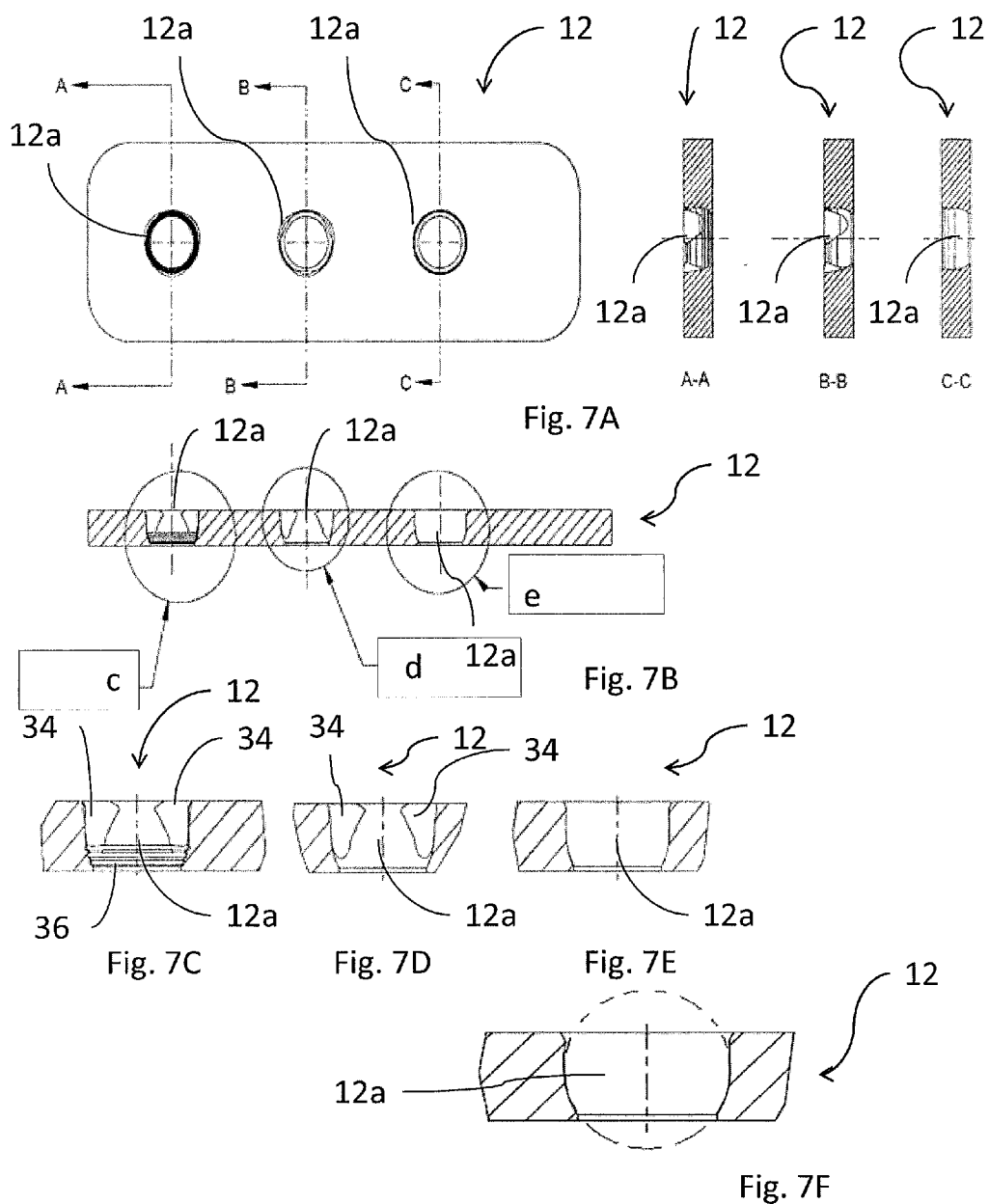

LOCKING SCREWS AND PLATES

CROSS-REFERENCE TO RELATED APPLICATIONS

This application is a U.S. national stage of International Patent Application PCT/US2012/029018 filed Mar. 14, 2012 entitled "Locking Screws and Plates", which claims the benefit of U.S. Provisional Patent Application No. 61/452,216 filed Mar. 14, 2011 entitled "Locking Bone Screws" and U.S. Provisional Patent Application No. 61/565,527 filed Dec. 1, 2011 entitled "Locking Bone Plate", all of which are incorporated by reference herein in their entirety.

BACKGROUND OF THE INVENTION

The present invention generally relates to locking screws and plates and in some particular embodiments, implantable locking screws and plates for securing to bone.

BRIEF SUMMARY OF THE INVENTION

In one embodiment there is a screw configured to be inserted into an aperture of a plate, the screw comprising, a head, a neck extending distally from the head and having a diameter, a shoulder extending distally from the neck and having a diameter, and a shaft extending distally from the shoulder and having a thread, a major diameter and a minor diameter, wherein the diameter of shoulder is larger than the diameter of the neck and larger than the minor diameter of the shaft.

In one embodiment, the shoulder includes a thread, a major diameter and a minor diameter. In one embodiment, the major diameter of the shoulder is larger than the diameter of the neck and larger than the major diameter of the shaft. In one embodiment, the minor diameter of the shoulder is larger than the diameter of the neck and is larger than the minor diameter of the shaft. In one embodiment, the minor diameter of the shoulder is larger than the diameter of the neck and is larger than the minor diameter of the shaft. In one embodiment, the diameter of the neck is less than the minor diameter of the shaft. In one embodiment, the diameter of the neck is generally equal to the minor diameter of the shaft. In one embodiment, the diameter of the neck is greater than the minor diameter of the shaft. In one embodiment, the shoulder is configured to snap fit through the aperture of the plate. In one embodiment, the neck is smooth. In one embodiment, the shoulder is smooth.

In another embodiment there is a plate comprising an aperture configured to receive a screw having a threaded shaft and a head and a locking bushing adjacent to the aperture, the locking bushing configured to receive a set screw, wherein screwing the set screw into the locking bushing expands the locking bushing radially into the aperture.

In one embodiment, the locking bushing is configured to prevent the head of the screw from rotating relative to the plate in a locked position. In one embodiment, the locking bushing is configured to prevent the head of the screw from disengaging from the aperture while allowing screw to pivot relative to the plate. In a further embodiment, the plate comprises the screw, a first torque being required to screw the screw into an object and relative to the plate while the shaft passes through the aperture and a second torque is required to screw the screw into the object and relative to the plate while the shoulder passes through the aperture, the second torque being greater than the first torque.

In another embodiment, a plate comprises an aperture configured to receive a screw having a threaded shaft and a head and an insert that partially extends into the aperture, the insert being made of a material that is softer than a material of the screw. In a further embodiment, the plate comprises the screw, a first torque being required to screw the screw into an object and relative to the plate while the shaft passes through the aperture and a second torque is required to screw the screw into the object and relative to the plate while the shoulder passes through the aperture, the second torque being greater than the first torque.

In one embodiment, the head of the screw includes one or more projections for engaging with the insert. In one embodiment, the one or more projections include a thread. In one embodiment, a pitch of the thread of the head is smaller than a pitch of the thread of the shaft.

In another embodiment there is a plate comprising an aperture configured to receive a screw having a threaded shaft and a head, the aperture having a convex inner wall configured to receive the head with a snap-fit. In a further embodiment, the plate comprises one or more relief sections extending radially outwardly from the aperture. In one embodiment, the one or more relief sections is semi-cylindrical. In one embodiment, the aperture includes one or more circumferentially extending grooves.

BRIEF DESCRIPTION OF THE SEVERAL VIEWS OF THE DRAWINGS

The foregoing summary, as well as the following detailed description of embodiments of the locking screws and plates, will be better understood when read in conjunction with the appended drawings of exemplary embodiments. It should be understood, however, that the invention is not limited to the precise arrangements and instrumentalities shown.

In the drawings:

FIG. 1 is a side elevational and partially cross sectional view of screws and a plate in accordance with an exemplary embodiment of the present invention;

FIG. 2A is a partial side cross sectional view of a screw and plate shown in FIG. 1 in an initial position;

FIG. 2B is a partial side cross sectional view of the screw and plate shown in FIG. 1 in a longitudinally locked position;

FIG. 4A is a top plan view of screws and a plate in accordance with an exemplary embodiment of the present invention in the radially locked position;

FIG. 4B is a partial side elevational and partially cross sectional view of the screws and plate shown in FIG. 4A;

FIG. 4C is a perspective top view of the screws and plate shown in FIG. 4A;

FIG. 7A is a top plan view and front cross sectional views of a plate in accordance with an exemplary embodiment of the present invention;

FIG. 7B is a side cross sectional view of the plate shown in FIG. 7A;

FIG. 7C is an enlarged view of the circled portion c in FIG. 7B;

FIG. 7D is an enlarged view of the circled portion d in FIG. 7B;

FIG. 7E is an enlarged view of the circled portion e in FIG. 7B;

FIG. 7F is an enlarged view of the circled portion e in FIG. 7B with a phantom circle illustrating the shape of the aperture.

DETAILED DESCRIPTION OF THE INVENTION

Figures 3A, 3B, 3C:
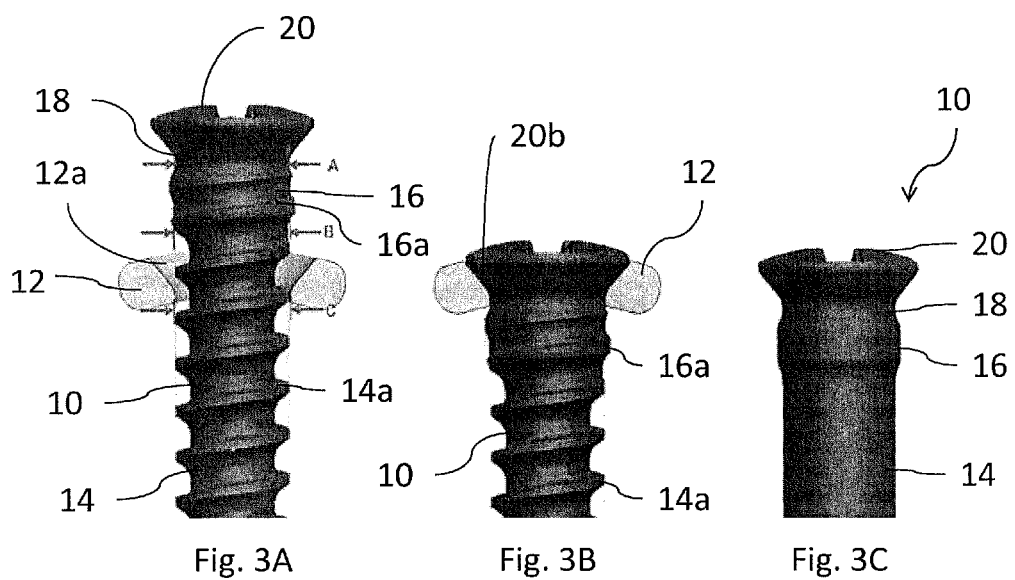
FIG. 3A is a partial side elevational view of the screw and plate shown in FIG. 1 in an initial position.
FIG. 3B is a partial side elevational view of the screw and plate shown in FIG. 1 in a longitudinally locked position.
FIG. 3C is a partial side cross section view of the screw and plate shown in FIG. 1 with the threads removed.
Figure 5A:
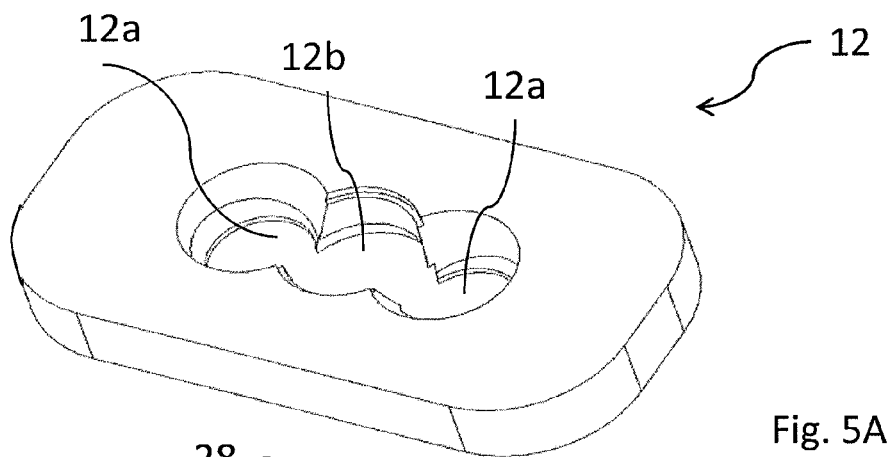
FIG. 5A is a perspective top view of the plate shown in FIG. 4A with the expandable locking bushing and set screw removed.
Figure 5B:
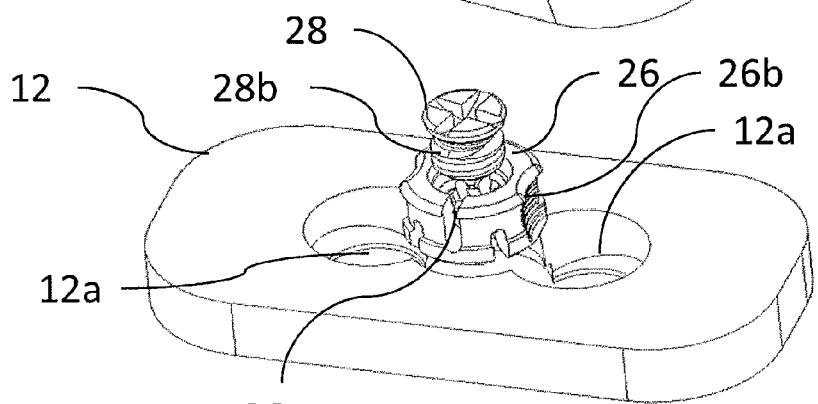
FIG. 5B is an exploded perspective top view of the plate shown in FIG. 4A.
Figure 5C:
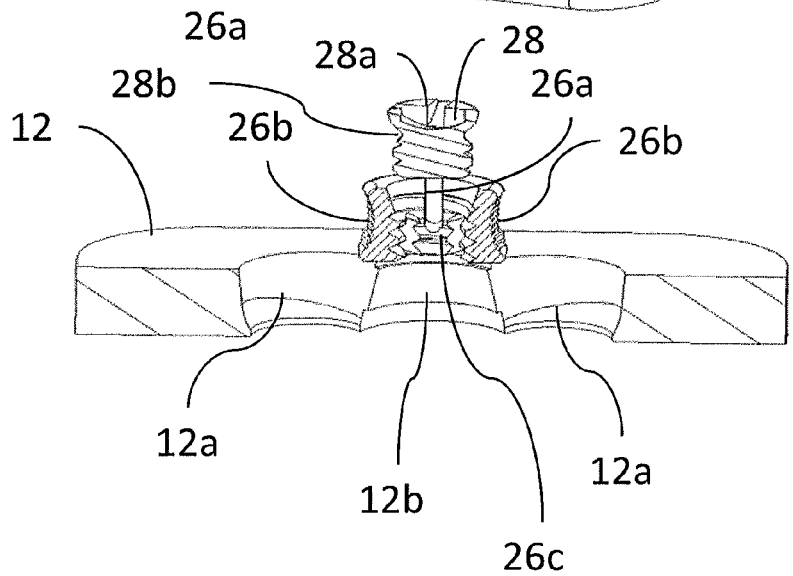
FIG. 5C is an exploded side cross sectional view of the plate shown in FIG. 4A.

In orthopedic surgery, it is common to rejoin broken bones. Screws, pins and plates are often used to extend across discontinuities in a bone to fix the broken ends in relation to one another to reduce pain and promote rapid healing without deformity. Plates are often secured to the bone by one or more screws driven into the bone.

In some instances, screws attaching the plate to the bone loosen over time, either relative to the bone or the plate or both. This is referred to as back-out. Severe back-out results in the bone screw working itself out of the bone and/or plate resulting in instability of the bone or joint. This situation results in increasing pain and danger from the instability, as well as, the movement of the screw.

Some known locking screws and plates allow the screw to lock relative to the plate but do not allow for the continued rotation of the screw relative to the plate once locked. Such a configuration prevents the plate from lagging with the bone once locked and may prevent a tight fit between the plate and the bone.

In some exemplary embodiments of the present invention, a screw 10 and a plate 12 are configured to allow screw 10 to lock relative to plate 12 in one or more directions (e.g., axially or longitudinally) but allow screw 10 to continue to move relative to plate 12 in one or more directions (e.g., rotate or pivot) once locked. In some embodiments, this allows screw 10 to continue advancing into the bone and lag the plate 12 with the bone. In some embodiments, this allows screw 10 to pivot relative to plate 12 such that the bones can move relative to one another (e.g., a spinal plate extending between two vertebrae). In some embodiments, plate 12 further or alternatively includes a locking mechanism that sets screw 10 in all directions once screw 10 and plate 12 are in the desired position.

Referring to FIGS. 1-8, screw 10 is configured to secure plate 12 to one or more objects. In a preferred embodiment, the one or more objects include bone (see FIG. 8 which discloses a volar pate). However, screws 10 and plates 12 described herein may be any size or shape and used in any application including non orthopedic applications such as carpentry.

Screws 10 and plates 12 described below and shown in FIGS. 1-8 may be comprised of any suitable material. In some embodiments, screws 10 and plates 12 described above are comprised of biocompatible materials. In one embodiment, screws 10 and plates 12 are comprised of biocompatible metal, such as stainless steel or titanium. In one embodiment, screws 10 and plates 12 are comprised of biocompatible polymer such as PEEK. In some embodiments, screws 10 and plates 12 are comprised of a combination of biocompatible metal(s) and polymer(s).

Referring to FIGS. 1-3B, plate 12 includes one or more apertures 12a each configured to receive a screw 10. Screw 10 includes a distal end 10a and a proximal end 10b. Screw 10 has a head 20 at the proximal end 10b. In one embodiment, head 20 includes a key 20a configured to engage a tool configured to deliver a torque to screw 10. In some embodiments, key 20a is an internal indent or external projection having any shape such as Torx, Phillips, slot, tri-wing, square or hex shaped.

Head 20 has an outer sidewall surface 20b that is configured to engage with the sidewalls of aperture 12a. In one embodiment, outer sidewall surface 20b of head 20 is frusta-conical in shape. In one embodiment, outer sidewall surface 20b is convex. In one embodiment, outer sidewall surface 20b of head 20 is semi-circular in shape. In one embodiment, outer sidewall surface 20b of head 20 is concave. In one embodiment, outer sidewall surface 20b of head 20 includes a thread. In one embodiment, the threads of head 20 are configured to match a corresponding thread of aperture 12a. In one embodiment, outer sidewall surface 20b of head 20 includes one or more grooves. In one embodiment, outer sidewall surface 20b of head 20 includes one or more projections. In one embodiment, the thread, grooves and or projections of outer sidewall surface 20b of head 20 are configured to lock into the aperture 12a and prevent rotation of screw 10 in a radially locked position as described below.

In one embodiment, screw 10 has a neck 18 that extends distally from head 20. In one embodiment, neck 18 is configured to allow free rotation of screw 10 when neck 18 is engaged with aperture 12a (see FIGS. 2B and 3B). In one embodiment neck 18 is smooth. In one embodiment, neck 18 is void of threads. In one embodiment, neck 18 is a rotated parabola in shape to form a concave surface. In one embodiment, neck 18 is configured to mate with aperture 12a to limit the amount screw 10 can pivot relative to plate 12 once engaged. In one embodiment, neck 18 is configured to mate with aperture 12a while allowing screw 10 to pivot relative to plate 12. In one embodiment, the diameter of neck 18 is substantially equal to the smallest diameter of aperture 12a. In one embodiment, the diameter of neck 18 is smaller than the smallest diameter of aperture 12a. In one embodiment, the diameter of neck 18 is slightly larger than the smallest diameter of aperture 12a.

In one embodiment, screw 10 has a shoulder 16 that extends distally from neck 18. In one embodiment, screw 10 has a shaft that extends distally from shoulder 16. In one embodiment, shoulder 16 is configured to require additional force to disengage neck 18 from aperture 12a than the force required to move a shaft 14 through aperture 12a. In one embodiment, shaft 14 includes a thread. In one embodiment, shoulder 16 includes a thread. In another embodiment, shoulder 16 is void of thread.

In one embodiment, shoulder 16 has a larger cross sectional dimension than a similar dimension of shaft 14 (see, for example, FIG. 3C). In one embodiment, the diameter of shoulder 16 is larger than the diameter of neck 18 and larger than the minor diameter of shaft 14. In one embodiment, the major diameter of shoulder 16 is larger than the diameter of neck 18 and larger than the major diameter of shaft 14. In one embodiment, the minor diameter of shoulder 16 is larger than the diameter of neck 18 and is larger than the minor diameter of shaft 14. In one embodiment, the minor diameter of shoulder 16 is larger than the diameter of neck 18 and is larger than the minor diameter of shaft 14. In one embodiment, the diameter of neck 18 is less than the minor diameter of shaft 14. In one embodiment, the diameter of neck 18 is generally equal to the minor diameter of shaft 14. In one embodiment, the diameter of neck 18 is greater than the minor diameter of shaft 14.

In use, in one embodiment, screw 10 is inserted into the appropriate aperture 12a and screwed into an object such as bone below plate 12 in an initial or insertion position (FIGS. 2A and 3A). In one embodiment, once aperture 12a reaches shoulder 16, the larger dimension of shoulder 16 than aperture 12a requires a greater force to get shoulder 16 through aperture 12a and in the longitudinally locked position (FIGS. 1, 2B, and 3B). In one embodiment, shoulder 16 is configured to snap fit through aperture 12a. In one embodiment, as screw 10 continues to advance into the object, the object will abut the bottom of plate 12 and in order for the screw to advance further, shoulder 16 must be pulled through aperture 12a. In one embodiment, if shoulder 16 is pulled through aperture 12a before the bottom of plate 12 contacts the object, the smooth neck allows screw 10 to continue to rotate relative to plate 12 even though screw 10 is locked axially or longitudinally relative to plate 12. This allows plate 12 to lag with the object and ensure that the object and plate 12 are properly secured once screw 10 is in the longitudinally locked position.

In one embodiment, a first torque is required to screw screw 10 into an object and relative to plate 12 while shaft 14 passes through aperture 12a and a second torque is required to screw screw 10 into the object and relative to plate 12 while shoulder 16 passes through aperture 12a, the second torque being greater than the first torque.

In some embodiments, screw 10 is not intended to be removed from plate 12 once in the longitudinally locked position. In one embodiment, screw 10 is subsequently releasably or permanently locked in the radial direction as described below. In one embodiment, screw 10 and plate 12 are removed from the patient together by unscrewing screw 10 from the object. In one embodiment, screw 10 is removeable from plate 12. In one embodiment, unscrewing screw 10 snap fits shoulder 16 back through aperture 12a. In one embodiment, the force required to pass shoulder 16 back through aperture 12a is greater than the force required to pass shoulder 16 through aperture 12a during installation. In one embodiment, the shape of shoulder 16 makes the shoulder easier to pass through aperture 12a during installation and more difficult during removal. In one embodiment, the distal end of shoulder 16 between shoulder 16 and shaft 14 is more sloped than a more abrupt proximal edge between shoulder 16 and neck 18. In one embodiment, shoulder 16 includes one or more depressible spring biased flanges that allow for aperture 12a to slide over during insertion and abut the bottom of plate 12 in the installed or longitudinally locked position. In one embodiment, shoulder 16 includes a sleeve comprised of a compressible material. In embodiments where the thread of shaft 14 continues over shoulder 16, shoulder 16 may be removed back through aperture 12a by applying sufficient torque to screw 10.

Referring to FIGS. 4A-7F, in some embodiments, there is a plate 12 that allows for screw 10 (that may or more not include one or more of the above features) to be locked in one or more directions relative to plate 12. In one embodiment, plate 12 makes it more difficult to rotate screw 10 relative to plate 12 than without. In one embodiment, the lock is releasable. In one embodiment, the lock is permanent. In some embodiments, the lock is radial and also acts as a longitudinal lock when twisting of screw 10 is required to move screw 10 relative to plate 12. In some embodiments, the radial lock includes an additional longitudinal lock such as the embodiments described above.

Referring to FIGS. 4A-5C, in one embodiment, plate 12 includes an expandable locking bushing 26. In one embodiment, locking bushing 26 is adjacent to aperture 12a and is configured to radially expand partially into aperture 12. In one embodiment, locking bushing 26 is generally cylindrical. In one embodiment, locking bushing 26 extends between two or more apertures 12a. In on embodiment, locking bushing 26 is positioned between one or more pairs of diametrically opposed apertures 12a. In one embodiment, a top portion of locking bushing 26 is configured to expand radially outwardly more than a corresponding bottom portion of locking bushing 26. In one embodiment, locking bushing 26 is split to allow for expansion from an initial position to the locked position. In one embodiment, locking bushing 26 is split partially along its axial length. In one embodiment, locking bushing 26 is split entirely along its axial length. In one embodiment, locking bushing 26 is spring biased towards its initial unlocked configuration. In one embodiment, locking bushing 26 expands equally in opposite directions.

Locking bushing 26 may be expanded radially to engage head 20 once screw 10 is put into a desired position. In one embodiment, locking bushing 26 retains screw 10 in place relative to plate 12. In one embodiment, locking busing 26 retains screw 10 in place relative to plate 12 in one or more directions. In one embodiment, locking bushing 26 sets or locks screw 10 relative to plate 12 in the axial and rotational directions. In one embodiment, locking bushing 26 sets or locks screw 10 relative to plate 12 in the axial direction while allowing screw 10 to rotate relative to plate 12. In one embodiment, locking bushing 26 sets or locks screw 10 relative to plate 12 in the axial direction while allowing screw 10 to pivot relative to plate 12.

In one embodiment, locking bushing 26 is configured to receive a set screw 28. In one embodiment, outer surface 28b of set screw 28 is threaded. In one embodiment, locking bushing 26 includes an internal thread configured to mate with the thread of set screw 28. In one embodiment, set screw 28 includes a key 28a configured to mate with a tool.

In one embodiment, locking bushing 26 has an outer surface 26b configured to engage outer surface 20b of head 20 in the radially locked position (FIGS. 4A-4C). In one embodiment, outer surface 26b is threaded. In one embodiment, outer surface 26b includes one or more grooves and/or projections. In one embodiment, locking bushing 26 and aperture 12a are configured to allow screw 10 to be positioned at a non-perpendicular or an acute angle relative to plate 12. In one embodiment, the angle of screw 10 relative to plate 12 may be varied before locking bushing 26 locks screw 10 relative to plate 12.

In one embodiment, locking bushing 26 is snap fit into plate 12. In one embodiment, locking bushing 26 includes one or more flanges or projections that engage into a groove in plate 12. In one embodiment, locking bushing 26 is integrally connected to plate 12. In one embodiment, locking bushing 26 is coupled to plate 12 by one or more fasteners. In one embodiment, locking bushing 26 is comprised of a different material than plate 12. In one embodiment, locking bushing 26 is comprised of a material softer than head 20 of screw 10.

In use, locking bushing 26 is configured to prevent or at least reduce the amount screw 10 rotates relative to plate 12 in a radially locked position. In one embodiment, once screw 10 is in the desired position relative to plate 12, set screw 28 is further inserted into locking bushing 26 to expand locking bushing 26 into aperture 12a, abut against surface 20b of screw 10 and reduce or prevent screw 10 from rotating relative to plate 12. In one embodiment, removing set screw 28 from locking bushing 26 allows for screw 10 to be removed from plate 12. In one embodiment, set screw 28 is partially inserted in locking bushing 26 in the initial or unexpanded position.

Figures 6A, 6B:
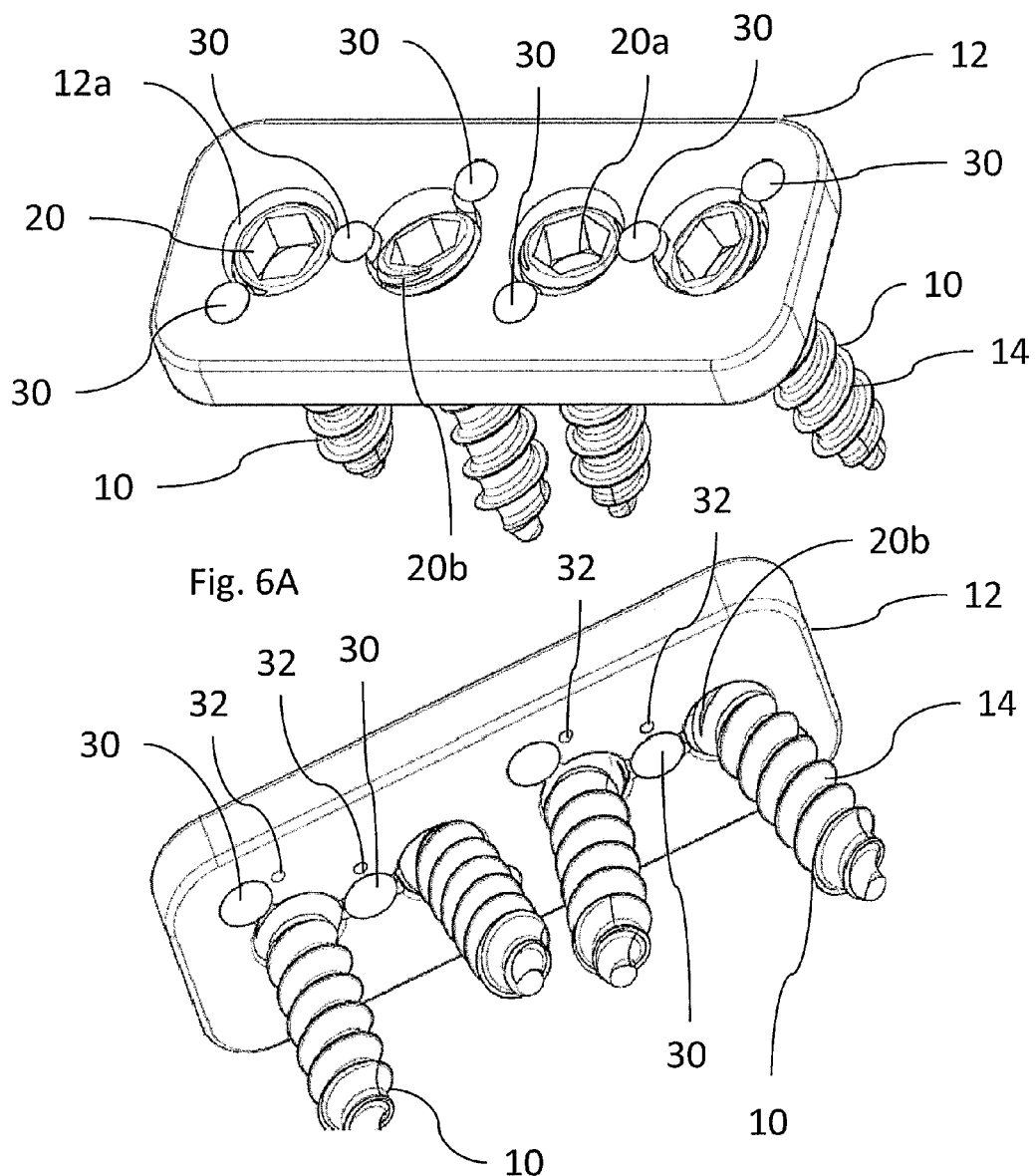
FIG. 6A is a perspective top view of screws and a plate in accordance with an exemplary embodiment of the present invention in the radially locked position.
FIG. 6B is a perspective bottom view of the screws and plate shown in FIG. 6A.
Figure 8:
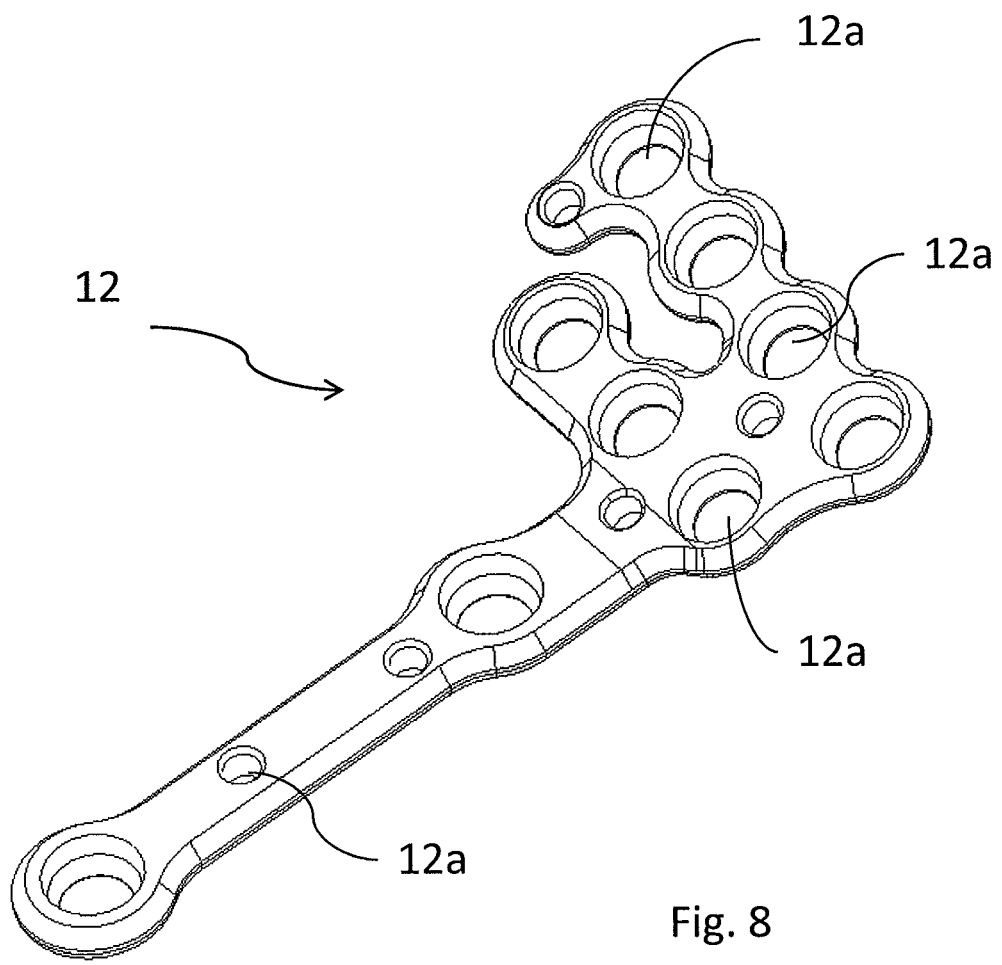
FIG. 8 is a perspective top view of a plate in accordance with an exemplary embodiment of the present invention.

Referring to FIGS. 6A and 6B, in one embodiment, plate 12 includes one or more inserts 30 that partially extend radially into an aperture 12a. In one embodiment, insert 30 allow screw 10 to be inserted into aperture 12a but then engage head 20 to reduce or prevent rotation of screw 10 relative to plate 12 in an installed position. In one embodiment, insert 30 jams a groove and/or projection on outer surface 20b of screw 10. In one embodiment, outer surface 20b of screw 10 includes a thread. In one embodiment, a pitch of the thread of head 20 is smaller than a pitch of the thread of shaft 14. In one embodiment, a pitch of the thread of head 20 is generally equal to the pitch of the thread of shaft 14. In one embodiment, outer surface 20b of screw 10 includes one or more circumferentially extending grooves and/or projections. In one embodiment, the threads, grooves and/or projections of outer surface 20b extend completely around head 20. In one embodiment, the threads, grooves and/or projections of outer surface 20b extend partially around head 20.

In one embodiment, insert 30 is comprised of a material that is softer than a material of screw 10. In one embodiment, insert 30 is comprised of a biocompatible polymer such as PEEK or a grade of Titanium or other biocompatible metal that is softer than the material of head 20. In one embodiment, one insert 30 extends into an aperture 12a. In on embodiment, two or more inserts extend into an aperture 12a. In one embodiment, one insert 30 extends into two or more apertures 12a. In one embodiment, inserts are generally cylindrical. In one embodiment, inserts 30 are any shape including conical, rectangle, convex or concave.

In one embodiment, insert 30 extends into aperture 12a more towards the bottom of aperture 12a than towards the top of 12a. In one embodiment, insert 30 is not tapered or is tapered less than the aperture 30 which tapers toward the bottom of plate 12. In one embodiment, head 20 of screw 10 becomes jammed or at least increases the amount of torque required to advance head 20 into aperture 12a. In one embodiment, once head 20 contacts insert 30 screw 10 continues to rotate and draw or lag plate 12 to the bone while head 20 is engaged with insert 30. In one embodiment, once head 20 and insert 30 are engaged the torque required to rotate screw 10 increases the further head 20 is advanced into aperture 12a.

In one embodiment, insert 30 is snap or compression fit into plate 12. In one embodiment, plate 12 is peened to retain insert 30 in plate 12. In one embodiment, one or more fasteners couple insert 30 to plate 12. In one embodiment, a groove or aperture 32 extends from the insert cavity and a portion or extension of insert 30 extends into aperture 32 to retain insert 30 relative to plate 12.

Referring to FIGS. 7A-7F, in one embodiment, plate 12 includes one or more apertures 12a configured to radially lock a screw 10 relative to plate 12. Though a single plate 12 is illustrated with three different aperture 12a embodiments, plate 12 may include any combination of aperture 12a types. In one embodiment, aperture 12a has a central diameter that is larger than top and bottom diameters. In one embodiment, aperture 12a is semi-spherical in shape (See FIG. 7F).

In one embodiment, a screw (not shown but may have a similar configuration to screws 10 described above) has a head configured to snap-fit into aperture 12a. In one embodiment, a first torque is required to advance the screw relative to plate 12 as the shaft of the screw is inserted through aperture 12a and a second torque is required to advance the screw relative to plate 12 and seat the head 20 of screw 10 in aperture 12a, the second torque being larger than the first torque. In one embodiment, the inside diameter of aperture 12a expands as the head 20 of screw 10 is seated in aperture 12a.

Referring to FIG. 7C and 7D, in one embodiment, aperture 12a may include one or more relief sections 34. In one embodiment, relief sections 34 are configured to allow the non relief sections to deform and expand into one or more of the relief sections 34. In one embodiment, relief sections 34 are equally spaced around the perimeter of aperture 12a. In one embodiment, aperture 12a includes three relief sections 34 equally spaced around the perimeter. In one embodiment, relief sections 34 are generally cylindrical in shape. In one embodiment, due to the shape of aperture 12a, relief sections 34 are larger toward the top of plate 12 than the bottom of plate 12. In one embodiment, relief sections 34 extend from the top of plate 12 past the middle of plate 12 but do not extend to bottom of plate 12. In one embodiment, relief sections 34 extend approximately 85% of the axial length of apertures 12a. In one embodiment, relief sections 34 extend the entire axial length of apertures 12a through the top and bottom surfaces of plate 12.

Referring to FIG. 7CA, in one embodiment, aperture 12a includes one or more circumferentially extending grooves 36. In one embodiment, grooves 36 are configured to have a tighter interference with projections or grooves in the head of a screw than the remainder of aperture 12a. In one embodiment, grooves 36 are configured to prevent or reduce longitudinal movement of the screw relative to plate 12 in an installed position. In one embodiment, grooves 36 are configured to prevent or reduce rotational movement of the screw relative to plate 12 in an installed or locked position. In one embodiment, grooves 36 are positioned in aperture 12a toward the bottom of plate 12.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. The words "right", "left", "lower" and "upper" designate directions in the drawings to which reference is made. The words "inwardly" and "outwardly" refer to directions toward and away from, respectively, the geometric center of the screw or plate. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

I claim:

1. A locking screw configured to be inserted into an aperture of a plate, the screw comprising: a head; a neck extending distally from the head and having a diameter; a shoulder extending distally from the neck and having a diameter; and a shaft extending distally from the shoulder and having a thread, a major diameter and a minor diameter, wherein the screw is configured to lock relative to the plate in a longitudinal direction after the shoulder is inserted through the aperture of the plate while being rotatable relative to the plate, wherein the shoulder includes a thread and a minor diameter, wherein the major diameter of the shoulder is larger than the major diameter of the shaft and the minor diameter of the shoulder is larger than the diameter of the neck and is larger than the minor diameter of the shaft, wherein the diameter of the neck is greater than the minor diameter of the shaft; the shoulder includes less than three crests in longitudinal profile, wherein the shoulder includes a rounded bulge configured to snap through the aperture in the plate.

2. The locking screw of claim 1, wherein the shoulder is configured to snap fit through the aperture of a plate.

3. The locking screw of claim 1, wherein the neck is smooth.

4. The locking screw of claim 1, wherein the screw is configured to not pivot relative to the plate when the shoulder is inserted within the aperture in the plate.

5. The locking screw of claim 1, wherein the aperture is shaped to correspond to the shape of the head.

6. The locking screw of claim 1, wherein the aperture and the head have a conical shape.

7. The locking screw of claim 1, wherein the aperture is concave and the shoulder is convex.

8. The locking screw of claim 1, wherein the aperture is configured to non-releasably retain the shoulder.

9. The locking screw of claim 1, wherein a distal end of the shoulder between the shoulder and the shaft is more sloped than a proximal end of the shoulder between the shoulder and the neck.

10. The locking screw of claim 1, wherein the shoulder includes one or more biased flanges.

11. The locking screw of claim 1, wherein the shoulder includes a sleeve comprised of a compressible material.

12. The locking screw of claim 1, wherein the shoulder is configured to snap-fit through the aperture of the plate.

13. The locking screw of claim 1, wherein the shoulder is configured to require additional force to drive the neck through the aperture in the plate than required to move the shaft through the aperture.

* * * * *